United States Patent [19]

McMichael et al.

[11] Patent Number: 5,395,751

[45] Date of Patent: Mar. 7, 1995

[54] ASSAY FOR CYTOTOXIC T CELLS

[75] Inventors: Andrew J. McMichael; Douglas F. Nixon; Frances M. Gotch, all of Oxford, Great Britain

[73] Assignee: United Biomedical, Inc., Hauppauge, N.Y.

[21] Appl. No.: 955,759

[22] PCT Filed: Jun. 14, 1991

[86] PCT No.: PCT/GB91/00963

§ 371 Date: Feb. 26, 1993

§ 102(e) Date: Feb. 26, 1993

[87] PCT Pub. No.: WO92/00524

PCT Pub. Date: Jan. 9, 1992

[30] Foreign Application Priority Data

Jun. 27, 1990 [GB] United Kingdom ............... 9014294

[51] Int. Cl.⁶ ................ G01N 33/569; G01N 33/577
[52] U.S. Cl. ..................................... 435/5; 435/7.24; 435/7.9; 435/30; 436/526; 436/548
[58] Field of Search .............. 435/4, 5, 7.21, 7.24, 435/7.9, 30; 436/526, 548

[56] References Cited

U.S. PATENT DOCUMENTS 4,554,088 11/1985 Whitehead et al. ............... 436/526

FOREIGN PATENT DOCUMENTS 0346022 12/1989 European Pat. Off. .
8605591 9/1986 WIPO .
8808538 11/1988 WIPO .

OTHER PUBLICATIONS

F. Sanchez–Madrid et al, Proc. Nat'l. Acad. Sci., USA, 79, 7489–7493, 1982.

*Primary Examiner*—David Saunders
*Attorney, Agent, or Firm*—Oblon, Spivak, McClelland, Maier, & Neustadt

[57] ABSTRACT

A method of detecting in a sample CTL specific for a particular virus, e.g. HIV, comprises contacting the sample with a support carrying immobilized antibodies to a surface antigen on T cells; separating the support and attached materials; contacting the separated support with target cells matched to the HLA type of the source of the sample and with HLA matched peptide epitope of the virus that interacts with the CTL of interest; and monitoring lysis of the target cells.

7 Claims, No Drawings

ASSAY FOR CYTOTOXIC T CELLS

FIELD OF THE INVENTION

This invention concerns an assay for cytotoxic T cells.

BACKGROUND OF THE INVENTION

Cytotoxic T cells (or cytotoxic T lymphocytes (CTL), as they are also known) are one of the types of cells that develop from lymphoid stem cells and that play an important role in the immune system. T cells are antigen specific, and carry antigen specific receptors. T cells also carry receptors for major histocompatability complex (MHC) proteins, and will only function in the presence of the relevant antigen and the appropriate MHC protein. Cytotoxic T lymphocytes interact with a target cell carrying the relevant antigen (e.g. a virus protein fragment on the surface of a cell infected with a particular virus) and also carrying the appropriate MHC Class 1 protein (or human leucocyte antigen (HLA) Class 1 molecule), and the CTL release cytotoxic enzymes which act to kill the target cell.

SUMMARY OF THE INVENTION

According to the present invention there is provided a method of detecting in a sample CTL specific for a particular virus, comprising contacting the sample with a support carrying immobilized antibodies to a surface antigen on T cells; separating the support and attached materials; contacting the separated support with target cells matched to the HLA type of the source of the sample and with HLA matched peptide epitope of the virus that interacts with the CTL of interest; and monitoring lysis of the target cells.

Any CTL in the sample will bind to the immobilised antibodies and hence the support, and will be separated from other material in the sample on separation of the support. Only CTL specific for the virus of interest will act to cause lysis of HLA matched target cells in the presence of the relevant peptide epitope, so that lysis of the target cells is indicative of the presence of the CTL of interest in the sample. By comparing results with those obtained from known standards a measure of the quantity of CTL in the sample can be obtained by monitoring target cell lysis.

The method has been shown to work well in detecting human immunodeficiency virus (HIV) specific CTL, using peptide fragments of HIV such as those disclosed in European Patent Specifications Nos. 0346022 and 0412766, and International Application No. PCT/GB91/00013. The invention is also applicable to detection of CTL specific for other viruses including HIV 1, HIV 2, related HIV viruses etc.

There is evidence that HIV specific CTL activity in patients infected with HIV varies with development of acquired immunodeficiency syndrome (AIDS) or related conditions: many healthy HIV seropositive patients have a vigorous anti-HIV CTL response, but there is evidence that HIV specific CTL activity declines as disease progresses. Measurement of HIV specific CTL in samples from patients infected with HIV may thus provide useful information in following disease progression.

The antibodies are conveniently immobilised in conventional manner on a suitable support as will be well known to those skilled in the art. The preferred support comprises a plurality of magnetic beads, such as Dynabeads (Trade Mark) produced by Dynal, Norway. The beads (and attached materials) are readily separated from a sample by magnetic attraction, providing an easy, simple separation technique.

The antibodies are preferably monoclonal antibodies, which may be produced using known techniques. Antibodies to any suitable T cell surface antigen may be used. The presently preferred antibody is monoclonal antibody to the CD8 marker on lymphocytes, but it will be clear that antibodies to other markers may also be used.

The sample may comprise, for example, suitable body fluid from a patient, such as blood, cerebrospinal fluid, lung fluid etc. Good results have been obtained in detection of HIV specific CTL in whole blood, without prior treatment or separation (e.g. of peripheral blood mononuclear cells). The technique can thus involve only a small number of processing steps, which is an advantage in infection containment and in reducing the risk of infection, e.g. with HIV.

The target cells are conveniently B cells, lymphoblasts, fibroblasts etc. The cells can be matched to the HLA type of the source of the sample using known techniques.

Lysis of the target cells is conveniently monitored by labelling the cells with a label released on lysis and monitoring released label One suitable label is $Cr^{51}$, but other radioisotopes, enzyme labels etc can also be used, as will be known to those skilled in the art.

The invention can thus provide a simple, readily performed assay that can be used, for instance, for detecting HIV specific CTL in whole blood.

The invention will be further described, by way of illustration, in the following example.

EXAMPLE

Materials and Methods

Blood samples were obtained from donor 007, who is a healthy HIV-seropositive haemophiliac attending the Oxford Haemophilia centre. His current CDC classification is CDC1. He was probably infected in 1984 by transfusion with HIV contaminated factor VIII.

10 mls of venous blood was put in a tube containing 0.1 ml of preservative free sodium heparin at 1000 units/ml. The blood was mixed with an equal volume of media RPMI 1640 (Gibco) supplemented with 100 units/ml penicillin and 200 ug/ml streptamycin in the absence of serum. Isolation of fresh peripheral blood mononuclear cells (PBM) was done by using standard lymphocyte separation methods, as described in EP 0346022.

For positive selection of CD8 or CD4 positive T cells, monoclonal antibody coated beads (Dynabeads M-450, prod. no 21001 and 11105 respectively, Dynal, Norway) were added to 10 mls of the blood media mixture in a target: bead ratio estimated as between 1:10–1:40 (100 ul beads added). The mixture was gently rotated for 10 minutes before being applied to a magnetic particle concentrator (Dynal). Positively selected cells were washed twice in RPM1 1640+10% fetal calf serum (abbreviated to 'R10'), resuspended in R10, and used directly as effector cells in a lysis assay.

Target cells were autologous B lymphoblastoid cell lines (BCL) incubated in the presence or absence of the HIV peptide fragment known as p24-14 at a final concentration of 50 uM. The peptide fragment p24-14 has the sequence $NH_2$-lysine-arginine-tryptophan-isoleucine-isoleucine-leucine-glycine-leucine-asparagine-lysine-isoleucine-valine-arginine-methionine-tyrosine-cysteine-COOH, and interacts specifically with HLA B27, as is described in EP 0346022. Specific lysis was measured in a 5 hr chromium release assay as described in EP 0346022 and in Nature, vol 336, 1988, pages 484–487.

Results

Blood from donor 007, mixed with an equal volume of media, was separated into three portions. One portion was separated on ficoll-hypaque and the PBM were used directly in the assay as fresh effectors. The other two portions were mixed with CD8+ or CD4+ Dynabeads as described. Effector cells were tested on autologous BCL target cells in the presence or absence of the peptide p24-14.

Freshly isolated PBM and the CD8+ selected population specifically lysed peptide treated targets. The CD4+ selected population did not. CD8+ dynabead selected effector cells from a CTL line or clone can also be used in the CTL assay.

On a separate occasion blood from donor 007 was mixed with CD8+ dynabeads and these cells were tested on autologous BCL targets, treated without peptide or with peptide p24-14. As a control, the cells were also treated on autologous BCL targets treated with the HIV peptide fragment known as p24-20: this fragment has the sequence $NH_2$-valine-glutamine-asparagine-alanine-asparagine-proline-aspartic acid-cysteine-lysine-threonine-isoleucine-leucine-lysine-alanine-leucine-tyrosine-COOH, and interacts specifically with HLA B8, as is described in British Patent Application No. 9000287.4. Again, specific lysis occurred on the peptide p24-14 treated target alone.

Discussion

Measurement of CTL activity has been more difficult than antibody assays due to the need for separated cells, the requirement for HLA matched targets and the need for appropriate antigens. Furthermore, for most vital systems studied there is a need to boost the number of CTL in vitro, usually by stimulation with virus.

CTL from a major part of the immune response to viruses and in HIV infection there is a remarkably strong anti-HIV specific CTL response. It is therefore possible to use directly isolated fresh PBM as an effector population in the CTL assay in some donors. There is some evidence that CTL activity declines with disease progression. There is therefore a need to measure anti-HIV specific CTL in larger cohorts of patients and relate this to clinical and other immunological parameters. The complexity of CTL measurement has hitherto allowed only specialist groups to measure it.

The positive selection of CD8+ cells from seropositive donors and their use in the CTL assay avoids the lymphocyte separation step. Not only is centrifugation unnecessary but there is less manipulation of the blood. Lysis of env infected targets by freshly isolated PBM from seropositive donors may be mostly due to non MHC restricted cell killing; selection of the CD8+ population allows partial identification of the effector phenotype, and will restrict measurement to MHC class 1 presented antigens. Further analysis of the fresh effector population may be possible using other monoclonal antibodies coupled to Dynabeads. As further peptide CTL epitopes become defined an assay based on target cells treated with HIV peptides from a set of common HLA antigens becomes possible and the serial assessment of large cohorts of patients for HIV specific CTL activity may reveal new understanding of this infection.

We claim:

1. A method of detecting in a sample the presence of cytotoxic T lymphocytes specific for a virus, comprising contacting said sample with a support carrying immobilized monoclonal antibodies to a CD8 surface antigen on T cells;
   separating said support and attached materials from the rest of said sample;
   contacting the separate support with target cells matched to the HLA type of the source of the sample and with an HLA matched peptide epitope of the virus that interacts with a cytotoxic T lymphocyte; and monitoring lysis of said target cells.

2. The method according to claim 1, wherein said support comprises a plurality of magnetic beads.

3. The method according to claim 1, wherein said sample comprises bony fluid from a patient, wherein said body fluid is blood, cerebrospinal fluid, or lung fluid.

4. The method according to claim 3, wherein said sample comprises whole blood.

5. The method according to claim 1, wherein said target cells are B cells, lymphoblasts, or fibroblasts.

6. The method according to claim 1, wherein lysis of said target cells is monitored by monitoring the release of a label from the cells.

7. The method according to claim 6, wherein said label is a radioisotope or an enzyme label.

* * * * *